United States Patent [19]

Blaas et al.

[11] Patent Number: 5,603,932
[45] Date of Patent: Feb. 18, 1997

[54] RECEPTOR OF THE MINOR HUMAN RHINOVIRUS RECEPTOR GROUP

[75] Inventors: Dieter Blaas; Ernst Kuechler, both of Vienna; Harald Mischak, Poelten; Christoph Neubauer, Vienna, all of Austria

[73] Assignee: Boehringer Ingelheim International GmbH, Ingelheim am Rhein, Germany

[21] Appl. No.: 636,722

[22] Filed: Apr. 23, 1996

Related U.S. Application Data

[62] Division of Ser. No. 450,684, May 25, 1995, which is a division of Ser. No. 182,824, Jan. 19, 1994, Pat. No. 5,447,840, which is a division of Ser. No. 95,246, Jul. 22, 1993, Pat. No. 5,304,636, which is a continuation of Ser. No. 294,512, filed as PCT/EP88/00312, Apr. 13, 1988, abandoned.

[30] Foreign Application Priority Data

Apr. 14, 1987 [DE] Germany .......................... 37 12 678.4

[51] Int. Cl.⁶ .................................................. A61K 39/00
[52] U.S. Cl. ..................................... 424/184.1; 424/159.1
[58] Field of Search .............................. 424/184.1, 159.1

[56] References Cited

U.S. PATENT DOCUMENTS 5,208,144  5/1993  Smith et al. ................................ 435/6

FOREIGN PATENT DOCUMENTS 0169146  1/1986  European Pat. Off. .

OTHER PUBLICATIONS

Marlin, et al., Nature, vol. 344, 6261 (70–72), 1990.
Condra, et al., J. Biol. Chem., vol. 265 (4), 1990, 2292–2295.
Abraham, G. and R. J. Colonno, "Many Rhinovirus Serotypes Share the Same Cellular Receptor," J. Virol. 51(2):340–345 (1984).
Abraham, G. and R. J. Colonno, "Characterization of Human Rhinoviruses Displaced by an Anti–Receptor Monoclonal Antibody," J. Virol. 62(7):2300–2306 (1988).
Beisiegel, U. et al., "Immunoblot Analysis of Low Density Lipoprotein Receptors in Fibroblasts from Subjects with Familial Hypercholesterolemia," J. Biol. Chem. 257(21):13150–13156 (1982).
Brown, M. S. and J. L. Goldstein, "A Receptor–Mediated Pathway for Cholesterol Homeostastis," Science 232:34–46 (Apr. 1986).
Chappell, D. A. et al., "The Low Density Lipoprotein Receptor–related Protein/α₂–Macroglobulin Receptor Binds and Mediates Catabolism of Bovine Milk Lipoprotein Lipase", J. Biol. Chem. (36):25764–25767 (1992).
Chatelet, F. et al., "Ultrastructural Localization by Monoclonal Antibodies of Brush Border Antigens Expressed by Glomeruli: II. Extrarenal Distribution," Am. J. Pathol. 122(3):512–519 (Mar. 1986).
Colonno, R. J. et al., "Isolation of a Monoclonal Antibody That Blocks Attachment of the Major Group of Human Rhinovruses," J. Virol. 571(1):7–12 (Jan. 1986).
Colonno, R. J. et al., "Human Rhinovirus Attachment Requires a Specific Cellular Receptor Protein," J. Cell Biochem. Suppl. 10 Part D:266 (Apr. 1986).
Colonno, R. J. et al., "Charaterization of the Cellular Receptor Specific for Attachment of Most Human Rhinovirus Serotypes," Virus Attachment and Entry into Cells, Crowell et al., eds., American Society for Microbiology: Washington, D.C. pp. 109–115 (Mar. 1986).
Colonno, R. J. et al., "Evidence for Direct Involvement of the Rhinovirus Canyon with Cellular Receptors," J. Cell Biochem. Suppl. 12 Part C:4 (1988).
Crowell, R. L. et al., "Relevance of studies of cellular receptors to the prevention and control of viral disease: Memorandum from a WHO Meeting," Bull. World Health Org. 63(6):1009–1012 (1985).
Davis, C. G. et al., "The J. D. Mutation in Familial Hypercholesterolemia: Amino Acid Substitution in Cytoplasmic Domain Impedes Internalization of LDL Receptors," Cell 45:15–24 (Apr. 1986).

(List continued on next page.)

Primary Examiner—Toni R. Scheiner
Attorney, Agent, or Firm—Sterne, Kessler, Goldstein & Fox P.L.L.C.

[57] ABSTRACT

A substantially pure receptor with binding activity for rhinoviruses of the minor human receptor group is disclosed, which has the following characteristics:

(a) a molecular weight of 120 kD on a polyacrylamide gel in the presence of SDS;
(b) a sedimentation constant, determined by sucrose gradient centrifugation in the presence of detergents, corresponding to about 28.4 S;
(c) is bound by *Lens culinaris* lectin;
(d) is not bound by heparin-sepharose;
(e) is bound irreversibly to an anion exchanger;
(f) has binding activity which is insensitive to neuraminidase;
(g) consists of sub-units connected by intermolecular disulfide bridges;
(h) shows no binding activity to rhinoviruses in the presence of EDTA; and
(i) has a binding activity to rhinoviruses which is only slightly influenced by iodoacetamide.

A receptor subunit of the above-described receptor, produced by complete reduction of said receptor, is also disclosed. Multimeric forms of the above-described receptor, obtained by controlled oxidation of the monomeric receptor, are also disclosed. Methods of providing protection against infection by rhinoviruses of the minor receptor group with the substantially pure receptor of the present invention, are also disclosed. A method for the production of receptors for the minor rhinovirus receptor group is also disclosed. A pharmaceutical composition and a method of treating rhinovirus infections in a subject is also disclosed.

3 Claims, 4 Drawing Sheets

OTHER PUBLICATIONS

Davis, C. G. et al., "Acid–dependent ligand dissociation and recycling of LDL receptor mediated by growth factor homology region," *Nature* 326:760–765 (Apr. 1987).

Goldstein, J. L. et al., "Coated pits, coated vesicles, and receptor–mediated endocytosis," *Nature* 279:679–685 (1979).

Hayden, F. G. et al., "Modification of experimental rhinovirus colds by receptor blockade," *Antiviral Res.* 9:233–247 (1988).

Herz, J. et al., "Surface location and high affinity for calcium of a 500–kd liver membrane protein closely related to the LDL–receptor suggest a physiological role as lipoprotein receptor," *EMBO J.* 7(13):4119–4127 (1988).

Hobbs, H. H. et al., "Polymorphism and evolution of *Alu* sequences in the human low density lipoprotein receptor gene," *Proc. Natl. Acad. Sci. USA* 82:7651–7655 (1985).

Hofer, F. et al., "The Low Density Lipoprotein Receptor Mediates Cell Entry of a Minor Group Common Cold Virus", unpublished.

Kerjaschki, D. and M. G. Farquhar, "The pathogenic antigen of Heymannn nephritis is a membrane glycoprotein of the renal proximal tubule border," *Proc. Natl. Acad. Sci. USA* 79:5557–5561 (1982).

Kerjaschki, D. et al., "Microdomains of Distinctive Glycoprotein Composition in the Kidney Proximal Tubule brush Border," *Cell Biol.* 97:178a Abstract 673 (1983).

Kerjaschki, D. et al., "Imunnoelectron microscopy in kidney research: Some contribution and limitations," *Kidney Internat.* 30:229–245 (Aug. 1986).

Kerjaschki, D. et al., "Identification of a 400–kd Protein in the Brush Borders of Human Kidney Tubules That Is Similar to gp330, the Nephritogenic Antigen of Rat Heymann Nephritis," *Amer. J. Pathol.* 129(1):183–191 (Oct. 1987).

Krah, D. L. and R. L. Crowell, "Properties of the Deoxycholate–Solubilized Hela Cell Plasma Membrane Receptor for Binding Group B Coxsackieviruses," *J. Virol.* 53(3):867–870 (1985).

Lonberg–Holm, K, and B. D. Korant, "Early Interaction of Rhinoviruses with Host Cells," *J. Virol.* 9(1):29–40 (1972).

Lonberg–Holm, K. et al., "Unrelated animal viruses share receptors," *Nature* 259:679–681 (1976).

Makker, S. P. and A. K. Singh, "Characterization of the Antigen (gp600) cof Heymann Nephritis," *Lab. Ivest.* 50(3):287–293 (1984).

McCray, J. and G. Werner, "Different rhinovirus serotypes neutralized by antipeptide antibodies," *Nature* 329:736–738 (Oct. 1987).

Mischak, H. et al., "Characteristics of the Minor Group Receptor of Human Rhinoviruses," *Virol.* 163:19–25 (1988).

Mischak, H. et al., "Detection of the Human Rhinovirus Minor Group Receptor on Renaturing Western Blots," *J. Gen. Virol.* 69:2653–2656 (1988).

Naruse, T. et al., "Laboratory Model of Membranous Glomerulonephritis in Rats Induced by Pronase–Digested Homologous Renal Tubular Epithelial Antigen," *Lab. Invest.* 33(2):141–146 (1975).

Noble–Harvey, J. and K. Lonberg–Holm, "Sequential Steps in Attachment of Human Rhinovirus Type 2 to Hela Cells," *J. Gen. Virol.* 25:83–91 (1974).

Raychowdbury, R. et al., "Autoimmune Target in Heymann Nephritis Is a Glycoprotein with Homology to the LDL Receptor," *Science* 244:1163–1165 (1989).

Rossmann, M. G. et al., "Structure of a human common cold virus and functional relationship to other picornaviruses," *Nature* 317:145–153 (1985).

Rossmann, M. G. and A. C. Palmenberg, "Convervation of the Putative Receptor Attachment Site in Picornaviruses," *Virol.* 164:373–382 (1982).

Russell, D. W. et al., "Domain Map of the LDL Receptor: Sequence Homology with the Epidermal Growth Factor Precursor," *Cell* 37:577–585 (1984).

Schneider, W. J. et al., "Purification of the LDL Receptor," *Meth. Enzymol.* 109:405–417 (1985).

Shepley, M. P. et al., "Monclonal antibody indentification of a 100–kDa membrane protein in Hela cells and human spinal cord involved in poliovirus attachment," *Proc. Natl. Sci. USA* 85:7743–7747 (1988).

Singh, A. K. and M. M. Schwartz, "Nephritogenicity and Immunocytochemical Localization of the 70–kilodalton Glycoprotein Subunit (gp70) of Heymann Antigen," *Clin. Immunol. Immunopathol.* 48:61–77 (1988).

Tomassini, J. E. and R. J. Colonno, "Isolation of a Receptor Protein Involved in Attachment of Human Rhinoviruses," *J. Virol.* 58(2):290–295 (May 1986).

Yamamoto, T. et al., "The Human LDL Receptor: A Cysteine–Rich Protein with Multiple Alu Sequences in Its mRNA," *Cell* 39:27–38 (1984).

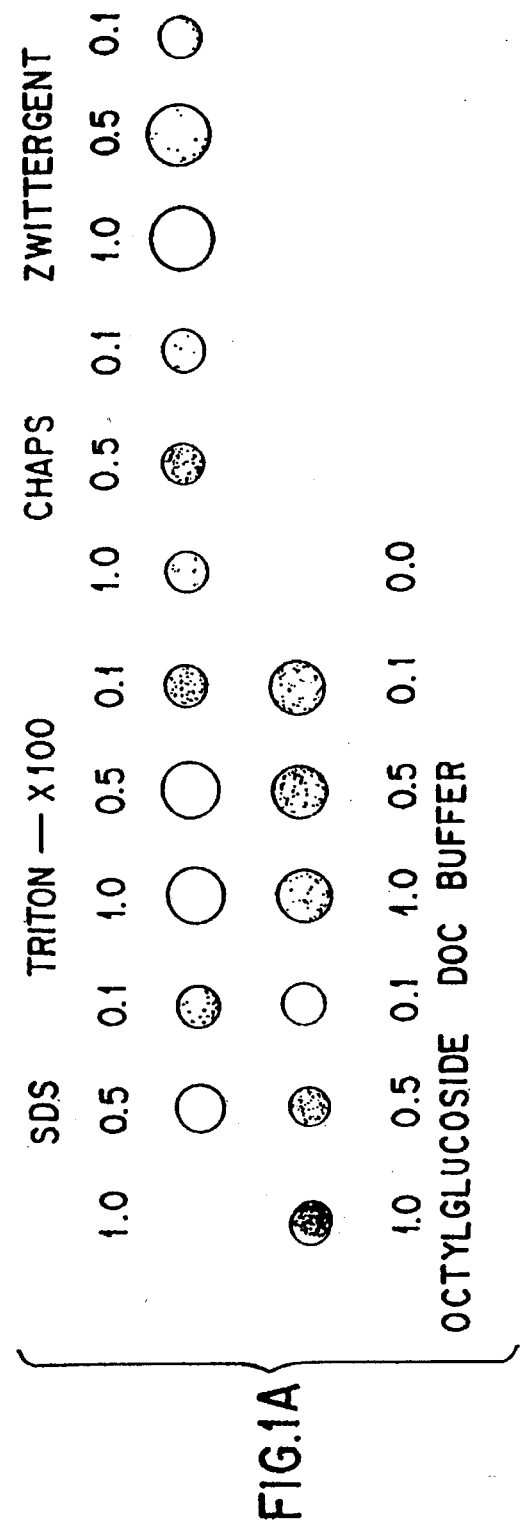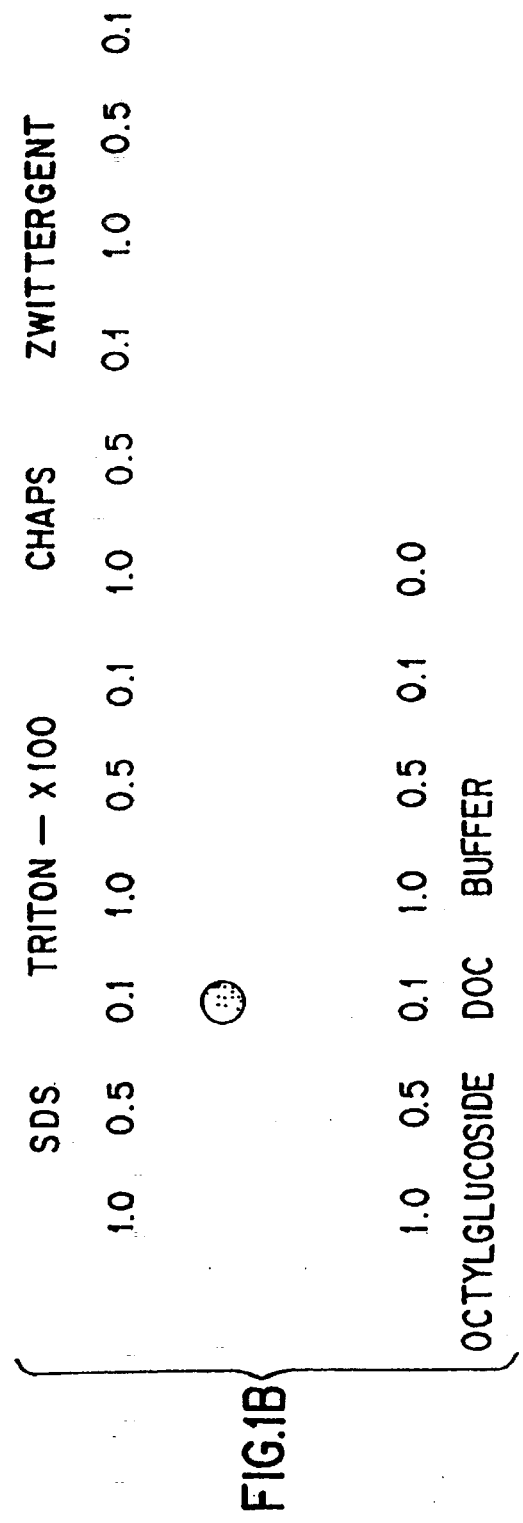

RECEPTOR OF THE MINOR HUMAN RHINOVIRUS RECEPTOR GROUP

CROSS-REFERENCE TO RELATED APPLICATIONS

This is a division of allowed U.S. application Ser. No. 08/450,684; filed May 25, 1995, which is a division of U.S. application Ser. No. 08/182,824, filed Jan. 19, 1994, issued as U.S. Pat. No. 5,447,840 on Sep. 5, 1995, which is a division of U.S. application No. 08/095,246, filed Jul. 22, 1993, issued as U.S. Pat. No. 5,304,636 on Apr. 19, 1994, which is a continuation of U.S. application Ser. No. 07/294,512, filed as PCT/EP88/00312, Apr. 13, 1988, abandoned. Priority to all foregoing U.S. applications is claimed under 35 U.S.C. § 120.

BACKGROUND OF THE INVENTION

1. Field of the Invention

This invention relates to the receptor of the small receptor group of human rhinoviruses, the purification and use thereof.

2. Brief Description of the Background Art

Human rhinoviruses constitute a large genus within the family of Picorna viruses and contain over 90 different serotypes Fox, J. P., *American J. Epid.* 103:345–354 (1976) and Melnick, J. L., *Proc. Med. Virol.* 26:214–232 (1980). These RNA viruses affect the respiratory tract of humans and cause acute infections which may lead to colds, coughs, hoarseness, etc., and are generally known as colds Stott, E. J. et al., *Ann. Rev. Microbiol.* 26:503–525 (1972). Infections caused by rhinoviruses are among the most common diseases in man. Although the course of the diseases is generally harmless, colds do nevertheless result in general weakening of the organism. This may then give rise to secondary infections caused by other pathogens.

The large group of human rhinoviruses can be subdivided into two sub-groups if the competition for binding sites on the cell surface in human cell culture cells (generally HeLa cells) is used as the criterion for classification. This original classification of a few representatives of the rhinoviruses Lonberg-Holm, K. et al., *Nature* 259:679–681 (1976) has been extended to 88 representatives as a result of a wide range of experiments Colonno, R. J. et al., *Journal of Virology* 57:7–12 (1986) and Abraham, G. and Colonno, R. J., *Journal of Virology* 51:340–345 (1984). The result of these experiments was to indicate that in spite of the large number, there are surprisingly only two different receptors on the cell surface to which representatives of one or other group of rhinoviruses can bind. Up till now, 78 serotypes of the large "rhinovirus receptor group" and 8 of the small "rhinovirus receptor group" have been classified (RVRG). 2 other representatives did not behave clearly so that they could not be definitively classified Abraham, G. and Colonno, R. J., *Journal of Virology* 51:340–345 (1984).

In recent years, a considerable increase in rhinovirus infections has been discovered in densely populated areas. Whereas the majority of other infectious diseases result in a long-lasting or permanent immunity from the pathogen in question, infections caused by rhinoviruses may recur again and again. The reason for the absence of any lasting immunity is the large variety of strains of rhinovirus which show little or no immunological inter-reaction with one another Fox, J. P. *Amer. J. Epidem.* 103:345–354 (1976) and Melnick, J. L., *Proc. Med. Virol.* 26:214–232 (1980). After infection has occurred, antibodies against the strain of virus in question can be detected but these do not confer any protection against other rhinovirus strains. In view of the large number of strains circulating in the population, repeated infections by rhinoviruses are possible.

Therefore, the presence of only two receptors offers promising possibilities for the successful combating of rhinoviral infections.

Since receptors are generally highly specific, there is a possibility of achieving controlled influence on the receptors by means of suitable substances, for example by blocking the receptors. If substances which block the receptor are used, the penetration of receptor-specific viruses into the cell can be prevented. The same substances which can prevent infection in this way can also be used for the treatment of a manifest rhinovirus infection. The production of such substances is made substantially easier and in some cases made possible for the first time, if the receptor in question is characterised.

SUMMARY OF THE INVENTION

One aim of this invention was therefore to isolate and purify the receptor for the small RVRG.

The only information on rhinoviral receptors available hitherto has concerned the receptor of the large RVRG.

The purification and characterisation of the receptor of the large RVRG was effected using a monoclonal antibody obtained by immunizing mice with HeLa cells. This receptor is glycosylated and has a molecular weight of about 440 kD in its native state; denaturing with sodium laurylsulphate results in a dissociation into subunits of 90 kD, leading one to conclude that the functional receptor is present as a pentamer Tomassini, J. E. and Colonno, R. J., *Journal of Virology* 58:290–295 (1986). Hitherto, the receptor for the small RVRG has neither been characterised nor purified. The only data on this receptor indicate its protein structure and also show that these or similar proteins are also present on cells in a number of other species. This distinguishes the receptor of the small RVRG essentially from the receptor of the large group, which has only been found in human cells and, in a few cases, in monkey cells. Influencing of this receptor, for example blocking the receptor with substances which prevent penetration of the virus into the cell, would appear to be suitable as a possible prevention or even treatment for an existing infection.

DETAILED DESCRIPTION OF THE INVENTION

The aim of this invention was therefore to provide the prerequisites for preparing substances which give protection against infections by rhinoviruses of the small receptor group.

This is achieved in the present invention by isolating the receptor from cell membrane, for example HeLa cell membranes. These cells were cultivated in suspension by methods known per se, the cells were broken up, the nuclei removed and the membranes purified. The receptors found in the membranes were then solubilized. To achieve optimum solubilization of active receptors from purified HeLa cells, various detergents were tested at different concentrations. The critical factor in choosing a specific detergent was its ability to solubilize as much membrane material as possible with the highest possible virus binding activity. 1% 1-O-n-octyl-B-D-glucopyranoside proved to be the most suitable (FIGS. 1A and 1B).

The insoluble constituents were removed and the receptors in solution were further purified. In order to be able to monitor the virus binding activity, a sensitive filter binding test was developed which makes it possible for $^{35}$S-labelled virus to bind to receptors which had been immobilized on nitrocellulose paper.

The viruses required for the test were cultivated and purified in a manner known per se Skern, T. et al., *Virology* 136:125–132 (1984).

The receptors according to the invention were purified by chromatographic methods.

Since it is known that the majority of membrane proteins are glycosylated, the receptor was purified on a *Lens culinaris* lectin column. This lectin has specificity for α-D-glucose and α-D-mannose units Young, N. M. et al., *J. Biol. Chem.* 271:1596–1601 (1971). Bound material was eluted with 1M α-D-methylglucoside in phosphate-buffered NaCl solution with 1% octylglucoside.

Aliquots were applied in duplicate to nitrocellulose and incubated both with native and with heated virus. Autoradiography of the fractions showed strong binding to the native virus in the case of the material which had been eluted, compared with the fractions from the material which had run through. The heated virus showed weak binding to the run-through material. This indicates nonspecific interactions which are caused by the high proportion of hydrophobic proteins;. heated rhinovirus has greater hydrophobicity Lonberg-Holm, K. and Whiteley, N. M., *Journal of Virology* 19:857–870 (1976). Since it had been established that, on being stored for a fairly long time at 4° C., purified virus gradually changes into particles which have the same antigenicity as heated virus (C-determinants), these contaminations were separated off by immunoprecipitation with C-determinant-specific monoclonal antibodies, for example mAK 2G2, immediately before the binding test was carried out. These monoclonal antibodies are obtained in a manner known per se by immunizing mice or rabbits with C-determinants and subsequently cloning according to Köhler and Milstein, *Nature* 256:495–497 (1975).

In addition to the *L. culinaris* lectin column, concanavalin A, ricin and heparin-Sepharose columns were also used to purify the receptor. The run-through and eluted material were tested as above. Con.A Sepharose columns were eluted with 1M α-D-methyl-mannoside, approximately 20% of the binding activity being recoverable; elution of the ricin column with 1M galactose resulted in approximately 100% recoverable binding activity. By contrast with the receptor for the Coxsackie B virus group Krah, D. L. and Crowell, R. L., *Journal of Virology* 53:867–870 (1985) heparin-Sepharose did not retard the binding activity.

The eluate from the *L. culinaris* column was separated on a Superose column by FPLC (Pharmacia) (gel permeation chromatography). By comparison with marker proteins, the molecular weigh-t of the active receptor was determined as 450 kD. At the same time, a substantial proportion of contaminating proteins could be removed (FIG. 2).

The minor group receptor migrates with an apparent molecular weight of 120 kD on the polyacrylamide gel in presence of SDS. Sometimes a barely visible band with a slightly lower molecular weight can also be observed which might represent a modification of the bulk of the receptor protein. The molecular weight of both forms of the receptor are considerably higher than found for the major group receptor (90 kD). As both proteins exhibit a molecular weight of about 450 kD in their native state it is not unlikely that their subunit structure is similar. The actual molecular weight might however differ from the one determined by gel permeation chromotography because of the small difference of retention volumes of proteins in this high molecular weight range. The picornavirus structure shows a deep depression (the canyon) running around the fivefold axes of icosahedral symmetry which is thought to contain the receptor binding site Rossman, M. G. et al., *Nature* 317:145–154 (1985). It has been proposed that the rhinovirus major group receptor and the receptor for the coxsackie B virus group Mapoles, J. E. et al., *Journal of Virology* 55:560–566 (1985) bind the virus at the five fold axes. The question whether the minor group receptor is a pentamer remains open as the molecular weight of its subunits is rather high when compared to the major group receptor.

By sucrose gradient centrifugation, it was possible to determine the sedimentation constant of the receptor. For this purpose, *L. culinaris* purified receptor was applied to a sucrose gradient and centrifuged.

The activity peak was found to be at the position of the gradient which corresponds to the sedimentation constant of 28.4 S (FIG. 3).

Preliminary tests had shown that the receptor could no longer be eluted from an anion exchange chromatography column. Since the receptor is insensitive to neuraminidase, sialic acid was removed from the glycoprotein in order to reduce the ionic interaction with the column material. The sample was then applied to a mono Q column (Pharmacia) and the receptor was eluted with an NaCl gradient. The binding activity could be detected as a broad peak at about 250 mM NaCl (FIG. 4).

It is also possible to purify the receptors according to the invention by a combination of chromatographic purification steps on different chromatography materials.

The chemical properties and structural requirements of the receptor according to the invention for vital binding were determined with the aid of enzymes and chemical reagents (Table 1).

Trypsin treatment destroys the binding activity entirely. This agrees with known results from enzymatic treatment of cell surfaces Stott, E. J. and Heath, G. F., *Journal of Gen. Virology* 6:15–24 (1970) and indicates the protein nature of the receptor.

Treatment of the solubilized receptor with neuraminidase resulted, in reproducible manner, in a slight increase in the binding activity. This treatment may possibly lead to better accessibility of the region on the receptor molecule which is the target of the virus interaction. As a result, sialic acid is not necessary for the virus binding.

Dithiothreitol (DTT) destroys the binding activity, leading one to conclude that disulphide bridges are involved in maintaining the correct folding of the protein. The surprisingly high molecular weight, determined by gel permeation chromatography and gradient centrifugation, indicates an oligomeric structure for the receptor molecule. The sensitivity to DTT might lead one to conclude that intermolecular disulphide bridges are necessary for the association of the hypothetical sub-units.

Treatment with iodacetamide reduces the binding activity only slightly and indicates that free sulphydryl groups are not necessary for efficient binding.

In the presence of ethylenediaminotetraacetic acid (EDTA) during incubation of the nitrocellulose filters with $^{35}$S-labelled virus, no binding could be detected. This agrees with earlier investigations which showed the need for the presence of divalent cations for interaction of the rhinoviruses with the cell surface Noble Harvey, J. and Lonberg-Holm, K., *Journal of Gen. Virology* 25:83–91 (1974).

Competitive binding assays between pairs of serotypes had been used in order to classify the human rhinoviruses into the two receptor classes Lonberg-Holm, K. et al., *Nature* 259:679–681 (1976) and Abraham, G. and Colonno, R. J., *Journal of Virology* 51:340–345 (1984). In the present invention, therefore, HRV2 and HRV49 were used as representatives of the small receptor group and HRV89 as representative of the large receptor group in competitive experiments to discover the specificity of the receptors according to the invention. The nitrocellulose filters with immobilized receptors were incubated in the presence of an approximately 20-fold excess of either HRV2 or HRV89 with labelled HRV2. As shown in Table 2, the binding was massively suppressed in the presence of non-labelled HRV2 but unaffected by HRV89. In order to check these results, the tests were repeated with labelled HRV49, using HRV2 and HRV89 as competitors. Once again, it is obvious that HRV2 reduces binding on a massive scale but HRV89 has no effect.

Although HRV2 and HRV89 bind to different receptors, their capsid proteins are surprisingly similar Duechler, M. et al., *Proc. Natl. Acad. Sci.* (in Press) (1987). A detailed comparison of structure between HRV2 and HRV14, based on the X-ray structure analysis of HRV14, was recently set up Blaas, D. et al., *Proteins* (in Press) (1987). Both HRV14 and HRV89 bind to the receptor of the large RVRG. It can therefore be expected that a cluster of preserved amino acids will be found at the hypothetical receptor binding site. Up till now, however, it has not yet been possible to discover a simple pattern of conservative amino acids within the Canyon region.

The present invention makes it possible for the first time to produce receptors for the small RVRG.

Using the receptors according to the invention it is possible for the first time to carry out controlled investigations on the virus/receptor interactions. Of particular importance is the locating of the regions on the receptors which are finally responsible for the vital activity. Once these areas are known, it should be possible to produce substances which are directed specifically against these areas, and thereby possibly block the receptors for a variety of different rhinoviruses.

The present invention relates to receptors which can be prepared by the process described and which bind representatives of the small RVRG.

The present invention also relates to the receptors which can be produced from the natural receptors by methods known to those skilled in the art. By way of example, there may be mentioned the sub-units of the natural receptor, which are obtained by treating with reducing agents, and which can be purified for example by electrophoretic methods. These sub-units may be used, for example, to produce polyclonal and/or monoclonal antibodies which can be used preparatively, diagnostically and/or therapeutically in a similar manner to the corresponding antibodies against the natural receptors. The receptor sub-units may also be used in a similar manner to the natural receptors.

The present invention also relates to the modifications of the natural receptors and/or the sub-units thereof which can be obtained by controlled enzymatic treatment. As has been shown in this invention, treatment with trypsin destroys the binding activity of the receptors according to the invention, while neuraminidase caused a slight increase in activity. Therefore it is conceivable, and anyone skilled in the art can check this in a non-inventive manner, that specific enzymes and/or chemical reagents result in receptors which either have an improved activity and/or are easier to apply and use and/or have better stability compared with the natural receptors. These modifications may, for example, result in parts of the protein chain being severed or cut out and/or the protein chains being cut up, in all or some of the sub-units of the natural receptors.

In addition to these modifications it is also possible to convert the natural receptors either wholly or partially into the sub-units, for example by controlled reduction. These large or small sub-units may also be linked together, for example by controlled oxidation, to form large or small units which are rearranged compared with the natural receptors.

Suitable reducing agents for cleaving disulphide bridges include, for example, thiol compounds such as thiophenol, 4-nitrothiophenol, 1,4-butanedithiol and particularly 1,4-dithiothreitol. The reduction is advantageously carried out in an aqueous/alkaline medium, for example in the dilute aqueous solution of an alkali metal hydroxide, e.g. sodium hydroxide, alkali metal carbonate, e.g. sodium carbonate or an organic base, more particularly a tri-lower alkylamine, e.g. triethylamine, at ambient temperature.

Suitable oxidizing agents for the re-linking of disulphide bonds in the reduced polypeptides include, for example, oxygen from the air, which is passed through an aqueous solution of the polypeptide to which a catalytic amount of a transition metal salt, e.g. iron(III)-sulphate, iron(III)-chloride or copper(II)-sulphate, may have been added; iodine, including iodine in the form of the potassium iodide adduct $KI_3$, which is preferably used in alcoholic, e.g. methanolic, or aqueous-alcoholic, e.g. aqueous-methanolic solution; potassium hexacyanoferrate(III) in aqueous solution; 1,2-diiodoethane or dimethyl or diethyl azodicarboxylate, which are reacted in water or in a mixture consisting of water and a water-miscible alcohol, e.g. methanol. Oxidation is more particularly carried out at ambient temperature.

The removal of the reagents, particularly the salts and the oxidants and reducing agents and their secondary products, from the desired compound is carried out by methods known per se, for example by molecular weight filtration, e.g. on Sephadex or Biogel.

All the modifications may be used in the same way as the natural receptors according to the invention. The products obtainable in this way, such as the antibodies, like the modifications, fall within the scope of the present invention.

The receptor according to the invention is soluble, so that it is easy to handle and use.

However, it is also possible to bind the receptors to a solid carrier and to use them in this form for diagnostic and preparative purposes. Suitable carriers include all the usual solid carriers such as polystyrene, glass, dextrans and also biological membranes and lipid vesicles.

It is also possible to bind conventional labels to the receptors and to use them in this form for diagnostic purposes. It is also possible to use the receptors for the therapeutic treatment of vital infections. If the receptors according to the invention are bound to a carrier, they may be used both diagnostically and also preparatively to bind the vital protein, for example by means of so-called affinity chromatography. Diagnostically, a vital protein can be detected in the usual way by a receptor bound to a carrier, e.g. by means of antibodies or labelled antibodies. The labelling used may be, for example, radioactive labelling, an enzyme or a fluorescent group.

When the receptors according to the invention are used therapeutically, they may be ejected in suitably highly refined-form, so that they can then inhibit competitively against the natural receptor. Preferably, soluble receptors will be used for this purpose. Such solutions may also be used for diagnosis and differential diagnosis.

An exceptionally important application is the use of the receptors according to the invention for producing polyclonal and/or monoclonal antibodies which act specifically against the receptors located in the cell membranes. Antibodies of this kind may first of all be used diagnostically to show up and determine the receptors on cells or biological cell material. Furthermore, they may be used therapeutically to block the receptors in the cell membranes. Consequently, they open up totally new methods and possibilities.

BRIEF DESCRIPTION OF THE DRAWINGS

FIG. 1A Filter binding test according to example 4. Receptor protein was applied to a nitrocellulose membrane. After saturation of nonspecific protein binding sites with 2% bovine serum albumin (BSA) in PBS-buffer the filter was incubated with $^{35}$S-methionine labeled native HRV2 in the presence of various detergents (SDS, Triton X-100, CHAPS, Zwittergent, Octylglycoside or DOC).

FIG. 1B Filter binding test showing a negative control. Corresponding filter binding test with $^{35}$S-methionine labelled denatured HRV2.

Figure 2:
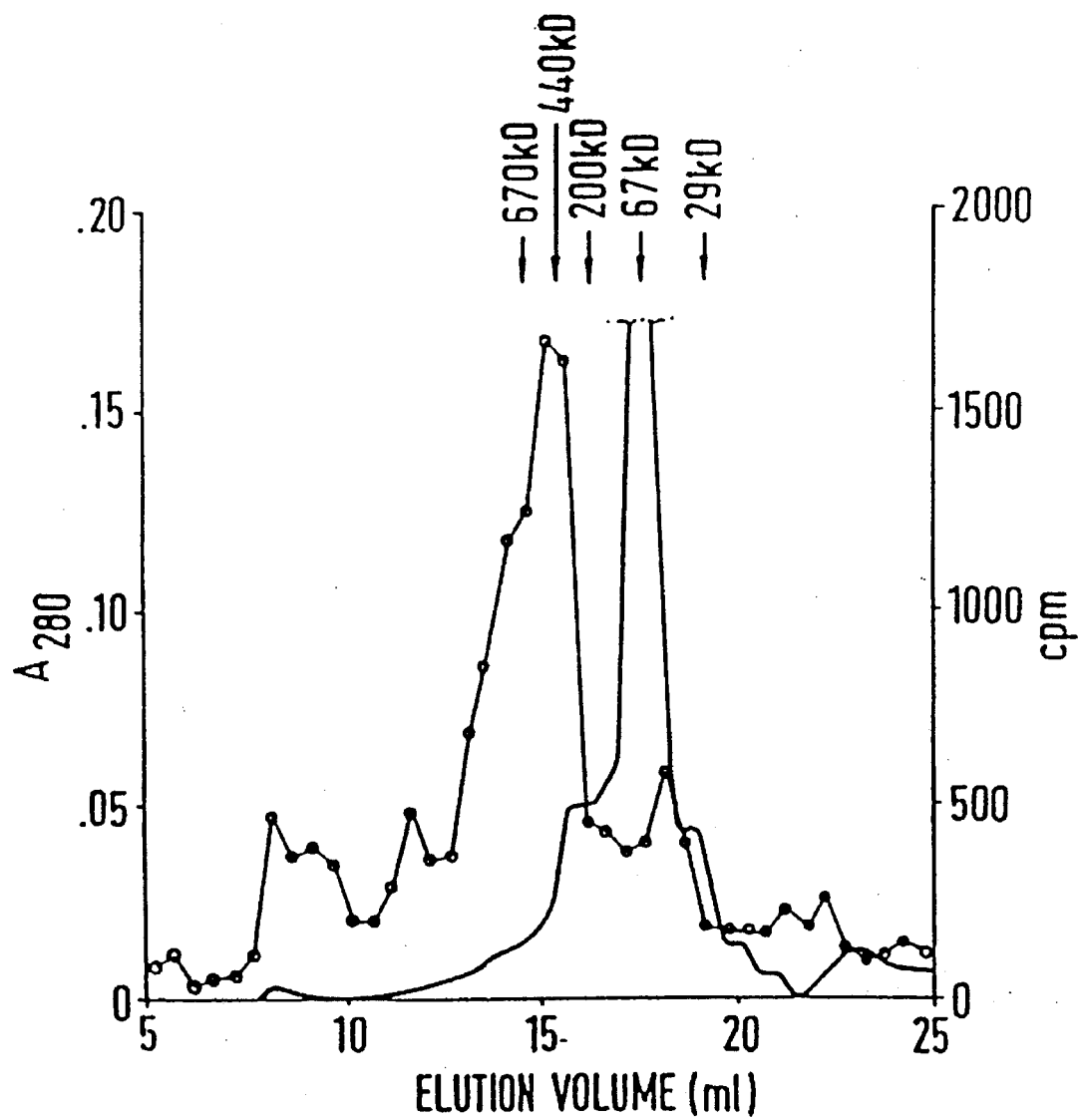
FIG. 2 Gel permeation chromatography of the solubilized receptor on a Superose 6 HR 10/30 column. Membranes equivalent to $10^8$ cells were solubilized in OG (15 mM sodium phosphate pH 7.4, 150 mM NaCl, 1 mM MgCl$_2$, 1 mM CaCl$_2$ (PBS) with 1% octyl glucoside), applied to a 1 ml L. culinaris column and the adsorbed material was eluted with 1M α-D-methylglucoside in OG. The eluate was concentrated in a Centricon test tube to 0.5 ml and applied to the Superose column. The column was developed with 0.2 ml/min OG and 0.5 ml fractions were collected. The binding activity of the individual fractions, the positions of the marker proteins (determined in a separate experiment) and the extinction at 280 nm are shown.

MATERIALS 1-0-n-Octyl-β-glucopyranoside, Tween 40 and 3-(3-cholamidopropyl)-dimethylammonio-1-propane sulphonate (CHAPS) were obtained from Sigma, N-tetradecyl-N,N-dimethyl-ammonio-3-propane sulphonate (Zwittergent 3–14) was obtained from Serra. The other detergents came from Merck, trypsin from Miles and $^{35}$S-methionine (1350 Ci/mmol) from Amersham.

EXAMPLE 1

Preparation of the Viruses

HRV2, HRV49 and HRV89 were cultivated essentially as described in HeLa cell suspension and then purified Skern, T. et al., Virology 136:125–132 (1984). The cultivation, isolation and purification of HRV2 will be described here by way of example.

HeLa cells (strain HeLa Ohio, 03-147, Flow Laboratories, England) were grown in suspension at 37° C. The suspension medium (Thomas, D. C., Conant, R. M. and Hamparian, V. U., 1970, Proc. Soc. Exp. Biol. Med. 133, 62–65; Stott, E. J. and Heath, G. F., 1970, J. Gen. Virol, 6, 15–24) consisted of a Joklik modification of MEM for suspension (Gibco 072-1300) and 7% horse serum (Seromed 0135). The inoculation density was $5$–$10\times10^4$ cells/ml and the volume was 500 ml. The suspension was centrifuged at a cell density of $1\times10^6$ cells/ml under sterile conditions at 300 g for 10 minutes. The supernatant was removed by suction filtering and the cells were resuspended in 100 ml of infection medium (Joklik modification of MEM for suspension culture with 2% horse serum and 2 mM MgCl$_2$). By carefully sucking up several times in a 20 ml pipette, the cells were homogeneously distributed in the infection medium. The medium was then made up to 500 ml. The cell suspension was brought to 34° C. and infected with HRV2 (twice plaque-purified) at a multiplicity of 0.1 viruses per cell. The HRV2 strain was obtained from the American Type Culture Collection, (ATCC VR-482 and VR-1112). The strain used was neutralized with antiserum against HRV2 (American Type Culture Collection, Cat.No. ATCC VR-1112 AS/GP). The control serum used was an antiserum against HRV7 (Cat.No. ATCC VR-1117 AS/GP) which showed no neutralization. After 60 hours at 34° C. the virus was harvested. Virus was obtained both from the cells and cell fragments and also from the medium.

For this purpose, the medium was separated from infected cells and cell fragments by centrifuging for 10 minutes at 1500 g and then suction filtering. The precipitate was frozen at −70° C.

The cell precipitates from 12 liters of suspension culture were combined, resuspended in 40 ml of TM buffer (20 mM Tris/HCl, pH 7.5, 2 mM MgCl$_2$), put on ice for 15 minutes, then broken up in a Dounce homogenizer and the mixture was centrifuged for 30 minutes at 6000 g. The precipitate was then washed once again in 10 ml of TM buffer. The two supernatents were combined and centrifuged for 3 hours at 110,000 g in order to pellet the virus. The virus pellet was then taken up in 10 ml of KTMP buffer (50 mM KCl, 50 mM Tris/HCl, pH 7.5, 5 mM MgCl$_2$, 2 mM mercaptoethanol, 1 mM puromycin, 0.5 mM GTP) and after the addition of 150 mcg of DNase I (Sigma, ribonuclease-free) it was incubated for 1 hour on ice.

The virus was precipitated from the infection medium with stirring at 4° C. with polyethylene glycol 6000 (PEG 6000; Merck) at a concentration of 7% and 450 mM NaCl (Korant, B. D., Lonberg-Holm, K., Noble, J. and Stasny, J. T., 1972, Virology 48, 71–86). After 4 hours in the cold, the virus was centrifuged off for 30 minutes at 1500 g, the precipitate was resuspended in 10 ml of KTMP buffer containing 75 mcg of DNase I, the mixture was incubated for 1 hour on ice and then frozen at −70° C.

The virus suspensions obtained from the cells and from the medium were combined, incubated for 5 min. at 37° C., cooled by the addition of 60 ml of cold TE buffer (10 mM Tris/HCl, pH 7.4, 1 mM EDTA) and then sonicated for 5 min in an ice bath.

The suspension was then centrifuged for 30 minutes at 6000 g. 920 ml of TE buffer containing 7% PEG 6000 and 450 mM NaCl were added to the supernatant, this was stirred carefully for 4 hours at 4° C. and the precipitate formed was pelleted for 30 minutes at 6000 g. The precipitate was once again taken up in 100 ml of TM buffer, the virus was precipitated as above by the addition of PEG 6000 and NaCl and pelleted. The precipitate was resuspended in 40 ml of TM buffer, the suspension was centrifuged for 30 minutes at 6000 g and the virus was pelleted for 3 hours at 110,000 g. The precipitate was dissolved in 1 ml TM buffer, incubated for 1 hour at 4° C. after the addition of 50 mcg of DNase I and then 1 ml of TE buffer was added. For further purification, the virus suspension was centrifuged on sucrose gradients (10–30% w/w in TE buffer) for 4 hours at 4° C. and at 110,000 g. From the extinction at 260 nm, the fractions containing the virus were discovered and diluted with TM buffer so that the final sucrose concentration was 10%. Then centrifuging was carried out for 8 hours at 85,000 g.

The virus pellet was taken up in 1 ml TM buffer and stored at −70° C. To check the purity of the virus preparation, electrophoresis was carried out on a 12.5% polyacrylamide gel in the presence of 0.1% sodium dodecylsulphate (Laemmli, U. K., 1970 Nature (London) 277, 680–685) and the protein bands were stained with Coomassie Brilliant Blue.

EXAMPLE 2

Preparation of $^{35}$S-methionine-labelled human rhinovirus serotype 2 (HRV2)

2 HeLa cell mono layers in 165 cm$^2$ Petri dishes were infected with an MOI (Multiplicity of Infection) of 40 with HRV2 for 1 hour at 34° C. in methionine-free MEM medium (Gibco) with 2% dialyzed fetal calf serum (Flow). The cells were washed twice with PBS and incubation was continued at 34° C. in fresh medium. After 3 hours, 1 mCi $^{35}$S-methionine (1350 Ci/mmol, Amersham) was added to each mono layer and incubation was continued for a total of 24 hours. The medium of infected cells and cell fragments was separated by 10 minutes' centrifuging at 1500 g and suction filtered. The precipitate was frozen at −70° C. in 5 ml of 10 mM Tris, 10 mM EDTA, pH 7.5 (Tris/EDTA) and thawed again. The supernatant and frozen/thawed precipitate were combined and centrifuged for 30 min. at 45,000×g. The supernatant from this centrifugation was centrifuged for 2 hours at 140,000×g. The virus pellet was resuspended in 300 mcl Tris/EDTA and the virus was purified over a 10–30% sucrose gradient as above. The individual fractions of the gradient were analysed by SDS electrophoresis in 12% polyacrylamide gels. The pure virus fractions were combined and stored in the presence of 1% BSA (bovine serum albumin) at 4° C. for at most 4 weeks. In order to remove virus with an altered capsid structure from the preparations from Examples 1 and 2, 20 mcl of immunoadsorbant, containing monoclonal antibodies against the C-determinant, for example mAK 2G2, were incubated with the purified virus for 30 min. and pelleted before the vital probes were removed.

Preparation of the Immunoadsorbant

*Staphylococcus aureus* (BRL) cells were suspended as a 10% w/w suspension in water. The cells were washed twice with PBS, ⅕ vol rabbit-anti-mouse IgG serum (Behring) was added; the suspension was incubated for 1 hour at ambient temperature. The cells were washed twice with PBS and incubated again for 1 hour with ⅕ vol mouse ascites fluid, which contained monoclonal antibodies against the C-determinants (e.g. mAK 2G2). After washing twice, it was pelleted, the pellet was resuspended in PBS (10% w/w) and the preparations of the radioactive viruses were added.

EXAMPLE 3

Solubilization of the receptor from HeLa cells

HeLa cells (strain HeLa-Ohio, 03-147, Flow Laboratories, England) were cultivated in suspension at 37° C. The suspension medium (Thomas, D. C., Conant, R. M. and Hamparian, V. U., 1970, Proc. Soc. Exp. Biol. Med. 133, 62–65; Stott, E. J. and Heath, G. F., 1970, J. Gen. Virol. 6, 15–24) consisted of a Joklik modification of MEM for suspension (Gibco 072-1300) and 7% horse serum (Seromed 0135). The inoculation density was 5–10×10$^4$ cells/ml and the volume was 500 ml. The suspension was centrifuged at a cell density of 1×10$^6$ cells/ml under sterile conditions at 300 g for 10 min. The supernatant was removed by suction filtering and the cells were washed twice with phosphate-buffered saline solution (PBS). 10$^9$ cells were suspended in 20 ml of isotonic buffer (10 mM HEPES-KOH, pH 7.9, 140 mM KCl, 1.5 mM MgCl$_2$, 0.5 mM EDTA, 0.2 mM phenylmethylsulphonylfluoride) and broken up in the cold with 200 pulses of a 50 ml Dounce homogenizer. Cell nuclei were removed by centrifuging for 3 minutes at 1000×g. The membranes were then further purified by the two-phase method Brunette, D. M. and Till, J. E., *J. Membr. Biol.* 5:215–224 (1971). Membranes corresponding to 2×10$^8$ cells per ml were taken up in PBS and stored in liquid nitrogen. To solubilize them, 2×10$^8$ cell equivalents were suspended in 1 ml of 1% octylglucoside in PBS (OG) and any insoluble material was removed by centrifuging at 80,000×g for 1 hour. The supernatant was used for column chromatography.

EXAMPLE 4

Filter Binding Test

Fractions from column chromatography to be tested for activity were applied to a nitrocellulose membrane (BA85, Schleicher and Schell) in a dot-blot apparatus (Bio-Rad). The probes were left to seep in at ambient temperature. Then liquid residues were suction filtered under a gentle water jet vacuum and non-specific protein binding sites were saturated with 2% bovine serum albumin (BSA) in PBS at 4° C. overnight. The filters were then incubated with 10$^5$ cpm $^{35}$S-methionine labelled HRV2 in 1% Tween 40, 0.5% sodium deoxycholate and 10 mM (3-(3-cholamidopropyl)-dimethylammonio-1-propane sulphonate) in PBS for 1 hour. The membranes were washed twice with 2% BSA in PBS, then dried and the round areas corresponding to the probes were stamped out; the radioactivity was measured in a liquid scintillation counter. As a specificity control, HRV2 was heated to 56° C. for 10 minutes before the incubation of the nitrocellulose filters Lonberg-Holm, K. and Yin, F. H., *Journal of Virology* 12:114–123 (1973). After this treatment, no binding to any of the probes could be detected (FIG. 1B). From this it was concluded that the binding of native HRV2 to the immobilized material can actually be ascribed to a specific interaction of the virus with the receptor.

EXAMPLE 5

Affinity Chromatography on *Lens culinaris* Lectin Columns

10$^8$ cell equivalents were solubilized as described and applied to an *L. culinaris* column (1 ml) equilibrated with OG. The column was washed with 5 ml of OG and bound material was eluted with 2 ml of 1M α-D-methyl-gluceside in OG. The binding test showed that almost 100% of the binding activity could be recovered, whereas about 90% of the total protein had been removed.

EXAMPLE 6

Gel Permeation Chromatography

The eluate from the *L. culinaris* column was concentrated down to 0.5 ml with a Centricon tube (exclusion 30 kD) and separated on a Superose 6 HR 10/30 column (equilibrated with OG-buffer) by FPLC (Pharmacia). By comparison with marker proteins the molecular weight of the active receptor could be determined as 450 kD. At the same time a large proportion of contaminating proteins could be removed (FIG. 2).

EXAMPLE 7

Sucrose Gradient Centrifugation

Figure 3:
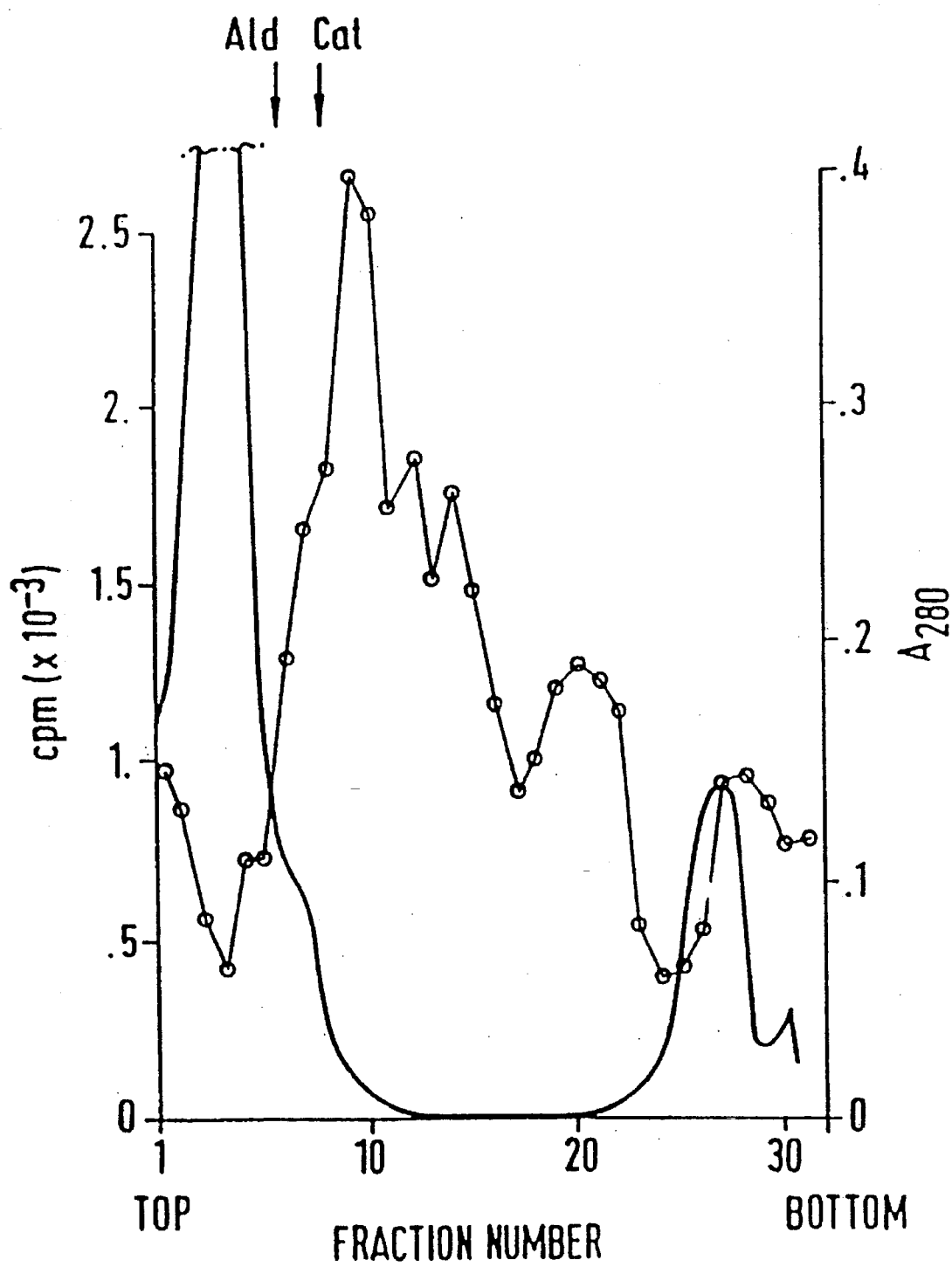
FIG. 3 Sucrose gradient centrifugation of the solubilized receptor. Material which had been eluted from an L. culinaris column was concentrated (see the legend to FIG. 2) and separated on a 10–40% sucrose gradient in OG. The binding activity of the fractions (0.4 ml), the position of the marker proteins catalase (Cat) and aldolase (Ald) and the extinction at 280 nm are shown.

*L. culinaris* purified receptor (as above) was applied to a sucrose gradient (10–40% in OG) and centrifuged for 8 hours at 38 krpm at 4° C. The activity peak was found at the position on the gradient corresponding to the sedimentation constant of 28.4 S. The positions of the marker proteins were determined in another gradient (FIG. 3). As a result of the presence of detergents, the markers sedimented at calculated sedimentation coefficients of 15.0 S and 21.9 S (7.3 S and 11.3 S in the absence of detergents).

EXAMPLE 8

Anion Exchange Chromatography

Figure 4:
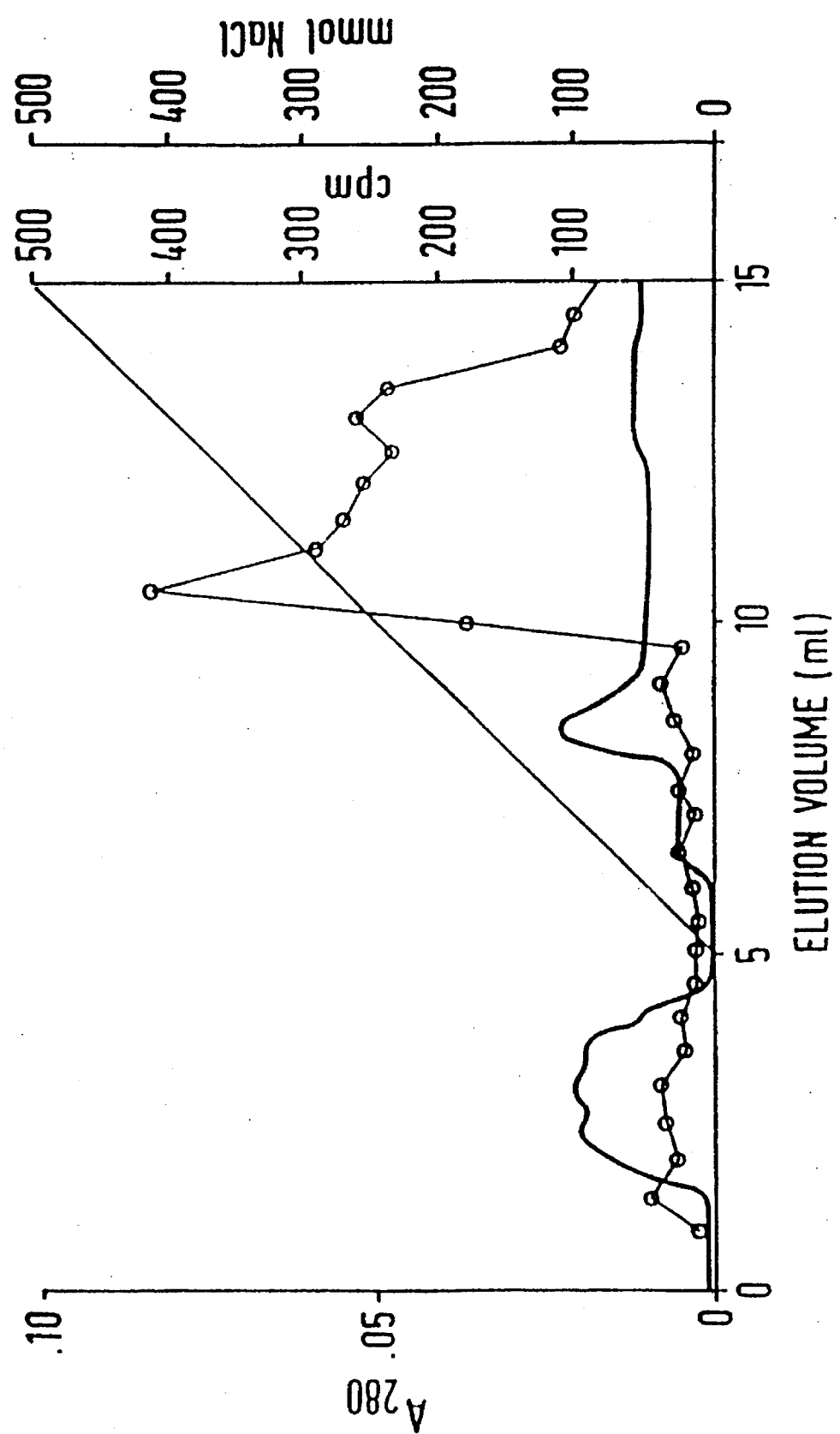
FIG. 4 Mono Q anion exchange chromatography. Fractions 14 to 16 of the gel permeation chromatography (FIG. 2) were treated with neuraminidase and the material was separated by FPLC on mono Q. The binding activity of the individual fractions (0.5 ml), the extinction at 280 nm and the path of the gradient are shown.

It had been found in preliminary tests that the receptor could no longer be eluted by mono Q HR 5/5 columns (Pharmacia). Therefore, receptor which had been subjected to preliminary purification using *L. culinaris* and gel permeation was treated with 1 U neuraminidase/mg of protein for 60 min at 37° C. in order to remove the strongly acidic neuramino acid groups. The sample was then diluted with 10 mM sodium phosphate buffer, pH 7, 1% octylglucoside, to twice the quantity and applied to a mono Q column. The column was developed with a gradient of 0 to 1M NaCl in the same buffer. The binding activity could be detected as a broad peak at about 250 mM NaCl (FIG. 4).

EXAMPLE 9

Isolation and Purification of the Receptor

Plasma membranes of $2\times10^9$ HeLa cells were solubilized in 5 ml PBS containing 1% w/v 1-0-n-octyl-β-D-glucopyranoside and 0.01% w/v each of L-α-p-tosyl-L-lysinechloromethyl ketone (TLCK), L-1-tosylamide-2-phenylethyl-chloromethyl ketone (TPCK), and phenylmethylsulohonylfluoride (PMSF) (all from Sigma) for 10 minutes at room temperature. Insoluble material was removed by centrifugation at 30 krpm for 30 minutes in the Beckman 65 fixed angle rotor. The supernatant was applied onto a 25 ml *L. culinaris* lectin column equilibrated with OG (PBS, 1% w/v octyl-glucoside) and bound material was eluted with 5 ml of OG containing 1M α-methyl glucose. The eluate was brought to 50% saturation by addition of the same volume of saturated ammonium sulfate. The precipitated material was dissolved in 2 ml of buffer A (10 mM Tris-HCl (pH 7.5), 5 mM EDTA, 1% w/v octyl-glucoside) and injected onto a Mono P anion exchange column connected to a Pharmacia FPLC system. The proteins were separated using a gradient from 0 to 100% buffer B (as A but containing 1.5M NACl). Fractions containing the virus binding activity were pooled, concentrated with a centricon tube to 0.5 ml and run on a Superose 6 column equilibrated with OG containing 5 mM EDNA. The protein concentration was monitored by the absorbance at 280 nm The fractions from this column were concentrated to 50 μl, made 0.1% w/v SDS and run in triplicate on a 6% polyacrylamide gel containing 5 mM EDTA Laemmli, U. K., *Nature* (London) 277:680–685 (1970). The proteins separated in the gel were then either stained with Coomassie blue or electrophoretically transferred to a nitrocellulose sheet Burnette, W. N., *Analytical Biochemistry* 112:195–203 (1981) which was incubated with $4\times10^5$ corn $^{35}$S - labelled HRV2 under conditions as described for the dot blots. The nitrocellulose was then dried and autoradiographed. As a control for specific binding an identical blot was incubated in presence of a 20 fold excess of unlabelled HRV2. It can be seen that fractions 6 and 7 from the Superose column contained material which was able to bind HRV2 when transferred to the nitrocellulose. The autoradiograph shows several bands with an apparent molecular weight greater than 300 kD in addition to one band at a position corresponding to approximately 120 kD when compared to protein markers run on the same gel. Only this 120 kD band disappears in the control containing excess unlabelled virus demonstrating specific interaction of this protein with HRV2. The polyacrylamide gel containing identical samples and stained with Coomassie blue shows a very faint band at a position corresponding to the radioactive band on the Western blot. This band is only found in the samples obtained from fractions 6 and 7 which exhibit virus binding activity.

EXAMPLE 10

Binding Tests

The restoration of an active receptor is dependent on mild conditions as boiling in SDS irreversibly destroys its activity. When the receptor preparation was incubated with 10 mM dithiothreitol prior to loading onto the polyacrylamide gel, no binding was observed. As the specific interaction of rhinoviruses with their receptors is dependent on the presence of divalent cations Noble-Harvey, J. and Lonberg-Holm, K., *Journal of Gen. Virology* 25:83-91 (1974) a blot obtained from a sample identical to the one applied onto lane 1 was incubated with virus in presence of EDTA. Under these conditions no binding could be observed. As further control an incubation of the nitrocellulose sheet with HRV2 which had been heated at 56° C. was carried out. This treatment leads to a structural change of the vital capsid which precludes recognition of the virus on the HeLa cell surface Lonberg-Holm, K. and Yin, F. H. *Journal of Virology* 9:29–40 (1973). No binding occurred under these conditions.

TABLE I

Sensitivity of the small rhinovirus group receptor

| Pretreatment of the solubilized small receptor group | Binding assay (% Bind.-act.) |
| --- | --- |
| No pretreatment | 100 |
| 10 mcg trypsin | 6 |

TABLE I-continued

Sensitivity of the small rhinovirus group receptor

| Pretreatment of the solubilized small receptor group | Binding assay (% Bind.-act.) |
| --- | --- |
| 50 mU neuraminidase | 170 |
| 10 mM dithiothreitol | 15 |
| 10 mM iodacetamide | 80 |
| 10 mM sodium periodate | 70 |
| 10 mM EDTA[a] | 5 |

All pre-incubations were carried out at 37° C. for 30 minutes.
Note:
[a] No pretreatment; instead, incubation was carried out with labelled HRV2 in the presence of 10 mM EDTA.

TABLE 2

Competition between various rhinovirus serotypes for the small receptor group.

| Competition of radioactively labelled HRV2 with: | Binding assay (% Bind.-act.) |
| --- | --- |
| nothing | 100 |
| HRV2 | 13 |
| HRV89 | 95 |
| Competition of radioactively labelled HRV49 with: | |
| nothing | 100 |
| HRV2 | 15 |
| HRV89 | 90 |

The filters were incubated with a 20-fold excess of non-labelled virus as described.

We claim:

1. A method of treating or preventing a rhinovirus infection in a subject, said method comprising administering to a subject in need of such treatment or prevention a receptor with binding affinity for the rhinoviruses of the minor human rhinovirus receptor group in an amount effective to treat or prevent said infection, wherein said receptor has the following characteristics:

(i) a molecular weight of 120 kD on a polyacrylamide gel in the presence of SDS;

(ii) a sedimentation constant, determined by sucrose gradient centrifugation in the presence of detergents, corresponding to about 28.4 S;

(iii) is bound by Lens culinaris lectin;

(iv) is not bound by heparin-sepharose;

(v) binds irreversibly to an anion exchanger;

(vi) has binding activity which is insensitive to neuraminidase;

(vii) consists of sub-units connected by intermolecular disulfide bridges; and (viii) shows no binding activity to rhinoviruses in the presence of EDTA.

2. The method of claim 1, wherein said treating is selected from the group consisting of ameliorating and curing.

3. The method of claim 2, wherein said subject is a human.

* * * * *